United States Patent
Drouilly et al.

(10) Patent No.: US 8,471,070 B2
(45) Date of Patent: Jun. 25, 2013

(54) METHOD OF CONVERTING ALCOHOLS IN THE PRESENCE OF A CATALYST OF PRETREATED ZINC OXIDE TYPE

(75) Inventors: Charlotte Drouilly, Maisons-Alfort (FR); Guylene Costentin, Carrier-sur-Seine (FR); Helene Lauron-Pernot, Paris (FR); Delphine Bazer-Bachi, Saint-Genis-Laval (FR); Celine Chizallet, Lyons (FR); Vincent Lecocq, Brignais (FR)

(73) Assignees: IFP Energies nouvelles, Rueil-Malmaison Cedex (FR); Centre National de la Recherche Scientifique, Paris Cedex (FR); Universite de Paris 6—Pierre et Marie Curie Laboratoire Reactivite de Surface, Paris Cedex (FR)

( * ) Notice: Subject to any disclaimer, the term of this patent is extended or adjusted under 35 U.S.C. 154(b) by 122 days.

(21) Appl. No.: 13/102,185

(22) Filed: May 6, 2011

(65) Prior Publication Data

US 2011/0288342 A1    Nov. 24, 2011

(30) Foreign Application Priority Data

May 7, 2010   (FR) ..................................... 10 01961

(51) Int. Cl.
*C07C 45/29*   (2006.01)
*C07C 45/38*   (2006.01)

(52) U.S. Cl.
USPC .......................................... 568/403; 568/487

(58) Field of Classification Search
USPC ........................... 568/403, 487; 585/535, 634
See application file for complete search history.

(56) References Cited

U.S. PATENT DOCUMENTS 4,141,919 A    2/1979   Gremmelmaier

FOREIGN PATENT DOCUMENTS

FR    2 377 367 A1    8/1978

OTHER PUBLICATIONS

Search Report of FR 1001961 (Dec. 9, 2010).
G. Djega-Mariadassou et al. "Dehydrogenation of Propan-2-ol on Zinc Oxide Powders as a Structure-Insensitive Reaction", J. Chem. Soc., vol. 78 (1982) pp. 2447-2454.

*Primary Examiner* — Sikarl Witherspoon
(74) *Attorney, Agent, or Firm* — Millen, White, Zelano & Branigan, P.C.

(57) ABSTRACT

The method for catalytic conversion of alcohols according to the present invention using a zinc oxide catalyst comprises a thermal pretreatment stage in an inert and/or reducing atmosphere at a temperature of at least 100° C., prior to the reaction stage.

9 Claims, 3 Drawing Sheets

METHOD OF CONVERTING ALCOHOLS IN THE PRESENCE OF A CATALYST OF PRETREATED ZINC OXIDE TYPE

FIELD OF THE INVENTION

The invention relates to a catalytic alcohol conversion method using a heterogeneous catalyst of zinc oxide type subjected to a thermal pretreatment stage in an inert and/or reducing gas atmosphere.

BACKGROUND OF THE INVENTION

Heterogeneous catalysis is widely used in the sphere of chemistry, notably in the petroleum industry or in biomass conversion, which is currently of increasing interest.

Zinc oxide is interesting as a catalytic active phase, most often for its basic properties. It is notably used in large-scale purification methods such as sulfur compound capture or it goes into the catalyst of the Esterfip-H® process developed by IFP, which involves vegetable oil transesterification reactions for biodiesel production.

Zinc oxide ZnO usually has a wurtzite structure, the zinc being surrounded by four oxygen neighbours. Under low dioxygen pressure, the compound becomes oxygen vacant and $Zn^{2+}$ ions occupy interstitial positions.

Conventionally, the reactivity of alcohols on acidic solids leads to dehydration and therefore to alkenes formation, whereas basic solids favour dehydrogenation reactions leading to aldehydes formation.

Mokwa et al. (Surface Science 117 (1982) 659-667) have studied the decomposition of ethanol under ultra-high vacuum on ZnO monocrystals and concluded that some faces are more active than others. Djega-Mariadassou et al. (J. Chem. Soc., Faraday Trans. 1, 19825, 78, 2447-2454) have studied the influence of the morphology of ZnO on the conversion of isopropanol. Prior to the reaction with isopropanol, the oxide is preheated under vacuum to 300° C. for 12 hours. The conversion kinetics of isopropanol has been studied on zinc oxides of different origins and it has been concluded that the morphology of the ZnO samples has a low impact on the catalytic properties of the dehydrogenation reaction. However, Halawy et al.'s results have shown that the ethanol decomposition reaction exhibits a different selectivity depending on the preparation mode. According to these various studies, it appears that effects related to the nature of the materials can explain reactivity differences. According to Perez-Lopez et al. (Materials Research Bulletin 40 (2005) 2089-2099), the catalytic properties of zinc oxide greatly depend on the size of the crystal, on the atmosphere in which the reaction is carried out since various tests have been conducted in air, hydrogen or nitrogen, and on the zinc salt precursor.

Teams are thus trying to improve the catalytic reactivity of ZnO and more particularly in alcohol conversion processes because of the current interest for biomass products.

The present invention comes within this scope since the inventors have surprisingly discovered that the conversion of alcohols to alkenes and/or oxygen compounds of alcohol type heavier than the initial alcohol, ketones, aldehydes, esters or acids, is markedly improved when the ZnO active catalytic phase is subjected to a thermal pretreatment in an inert and/or reducing atmosphere.

SUMMARY OF THE INVENTION

The present invention relates to an alcohol conversion method wherein the zinc oxide used as the catalytic active phase undergoes a thermal pretreatment in an inert and/or reducing atmosphere.

DETAILED DESCRIPTION

Figure 1:
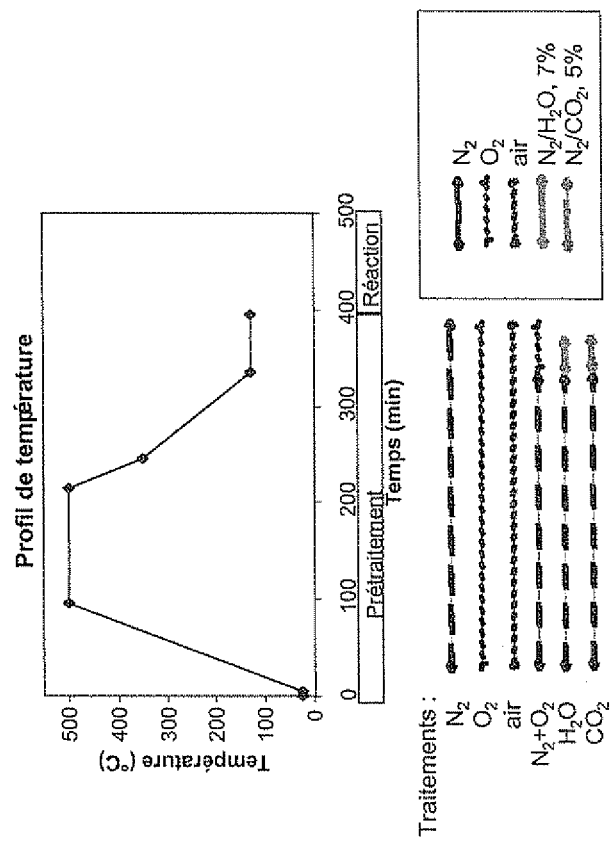
FIG. 1 shows the temperature profile during pretreatment.

The catalytic alcohol conversion method according to the present invention using a zinc oxide-based catalyst comprises a thermal pretreatment stage in an oxygen-free inert and/or reducing atmosphere, at a temperature of at least 100° C., prior to the reaction stage.

Thus, the conversion of alcohols is markedly improved by means of the thermal pretreatment carried out on the zinc oxide. The catalytic activity of the zinc oxide is increased as a result of the pretreatment in an inert and/or reducing atmosphere.

What is referred to as a reducing atmosphere relates to conditions wherein oxidation is prevented by elimination of the oxygen or of other oxygen-containing gases or vapours, and to a greater extent of any gas having oxygen atoms in its structure. In most cases, it is an atmosphere of hydrogen or of substances that readily release electrons.

What is referred to as an inert atmosphere is a non-reactive gas atmosphere.

Preferably, pretreatment is carried out in an atmosphere of nitrogen, argon and/or hydrogen. It is essential that the atmosphere in which the thermal pretreatment is conducted is free of oxygen.

The temperature rise up to the so-called pretreatment temperature is achieved by means of a heating ramp of about 5° C./min.

The thermal pretreatment is carried out at a temperature of at least 100° C. It is preferably carried out at a temperature of at least 300° C.

More preferably, the thermal profile of the pretreatment stage comprises at least one step at a temperature of 500° C., for at least 60 minutes, then a temperature descent down to the alcohol conversion reaction temperature.

Generally, the reaction temperature ranges between 100° C. and 500° C. This temperature preferably ranges between 200° C. and 450° C., and more preferably between 300° C. and 400° C.

The temperature descent rate is imposed by the inertia of the oven in which the pretreatment is performed, it is of the order of 3° C./min.

The alcohols used in the method according to the present invention are primary, secondary or tertiary alcohols. The alcohol can for example be 2-methylbut-3-yn-1-ol.

More preferably, the alcohol is ethanol.

The zinc oxide used in the method according to the present invention can be commercial zinc oxide ZnO, for example the ZnO known as Kadox, marketed by the Horsehead Company and prepared by combustion of metallic zinc.

The zinc oxide can also be obtained by thermal decomposition of precursors, whether commercial or obtained by preliminary precipitation. The thermal decomposition of an organic zinc salt selected from among zinc nitrate, zinc carbonate, zinc acetate, zinc citrate, zinc oxalate and/or zinc hydroxynitrate can be mentioned for example. Thermal decomposition is achieved by calcination in air.

The zinc oxide can also be prepared by sol-gel processes/solution chemistry, precipitations, complexations, hydrothermal processes, solvothermal processes, CVD or any other technique known to the person skilled in the art.

The products obtained after alcohol conversion according to the method of the present invention are alkenes and/or oxygen compounds of alcohol type heavier than the initial alcohol, ketones, aldehydes, esters or acids.

If the alcohol is ethanol, acetaldehyde and/or ethylene and often condensation products are generally obtained.

The alcohol conversion yields, given in percentage, are calculated according to the following formula:

$$Conv = \frac{A°_{alcohol} - A_{alcohol}}{A°_{alcohol}} \times 100$$

where $A°_{alcohol}$ is the surface area given by the chromatogram, relative to the alcohol, prior to contacting the catalyst, and $A_{alcohol}$ is the surface area relative to the alcohol after contacting with the ZnO sample.

The examples hereafter illustrate the invention without limiting the scope thereof.

EXAMPLES

The conversion method according to the present invention was implemented with 2-methylbut-3-yn-1-ol (MBOH).

Example 1

A sample of commercial Kadox type ZnO was tested. This product has a specific surface area of 9 m²/g.

Various types of pretreatment were carried out on this sample.

The treatments in a stream follow the temperature profile given in FIG. 1.

The thermal treatment can be carried out in a stream of $N_2$ (according to the invention) or of $O_2$ or of air, by way of comparison. The gas flow rate during pretreatment is 20 mL/min.

The device comprises a supply zone and a gas orientation zone, the reaction zone comprises the reactor containing the zinc oxide sample, and the analysis zone allows to identify the reaction products.

The reactant (MBOH) is injected from the supply zone, from a saturator maintained at 20° C. The carrier gas, dinitrogen, bubbles into the methylbutynol at a flow rate of 50 mL·min$^{-1}$. The partial pressure is then 1.73 kPa. The pure dinitrogen, the pure dioxygen or industrial air at 20 mL·min$^{-1}$ acts as a catalyst pretreatment gas. A valve box heated at 100° C. allows to orient the reactive gas towards the sample during the reaction period, or directly towards the analysis system during ZnO pretreatment.

50 mg catalyst are deposited on the sintered glass of a 10 mm-diameter Pyrex reactor and heated by means of a vertical tubular oven. Temperature control is provided by a thermocouple connected to a programmer.

The alcohol used (MBOH) decomposes into equimolar amounts of acetone and acetylene. The products are subjected to an on-line analysis using a gas chromatograph of microGC type equipped with a CPWAX 52 CB column.

Prior to contacting the zinc oxide with the methylbutynol, a pretreatment stage allows to activate it by removing the water and optionally the carbon dioxide adsorbed at the surface: it consists in a 5° C.·min$^{-1}$ temperature rise up to the pretreatment temperature (500° C.) that is maintained for two hours in dinitrogen (according to the invention), oxygen or air (not in accordance with the invention) at 20 mL·min$^{-1}$. Oxygen, $CO_2$, water or ethanol can then be adsorbed. Adsorption lasts for ten minutes. The nitrogen at 20 mL·min$^{-1}$ carries along 1 mL·min$^{-1}$. $CO_2$ or chilled water, or ethanol at 20° C.

The temperature profile is shown in FIG. 1.

Between the pretreatment and the start of the reaction, the temperature descent occurs at the rate of inertia of the oven (about 3° C.·min$^{-1}$). The reaction temperature (130° C.) is selected so as to obtain adequate conversions, i.e. not too high (below 30%) for fear of diffusion limitations.

Figure 2:
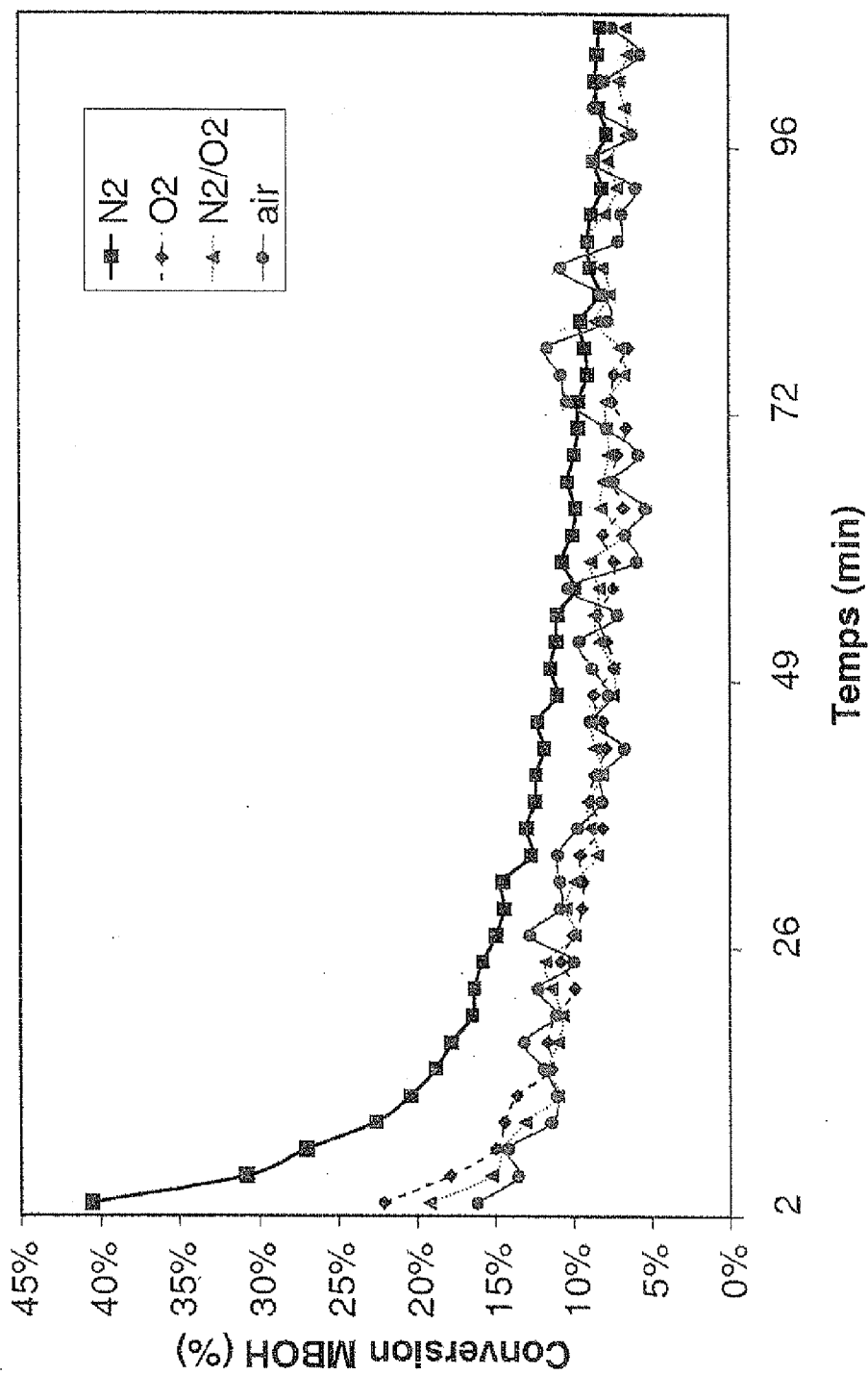
FIG. 2 gives a comparison of the conversion profiles of 2-methylbut-3-yn-2-ol as a function of time for ZnO samples of commercial Kadox type, pretreated at 500° C. in $N_2$, $O_2$, $N_2/O_2$ or in air.

The MBOH conversion profiles as a function of the reaction time for Kadox ZnO samples pretreated in $N_2$, $O_2$, $N_2/O_2$ or in air are given in FIG. 2.

It can be observed that the initial conversion to the first point, measured after two minutes in a reactant stream, of the sample that has been subjected to a pretreatment at 500° C. in nitrogen exclusively is 41%, whereas the conversions pretreated in the presence of oxygen are 22% maximum.

Example 2

A ZnO sample resulting from the thermal decomposition of the zinc carbonate (calcination for two hours at 500° C. in air) was tested. This product has a specific surface area of 22 m²/g and the colour is more yellow than the sample used in Example 1, this colour being characteristic of a larger proportion of vacancy type defects.

The same pretreatments as those performed in Example 1 are carried out on this ex-carbonate sample.

Figure 3:
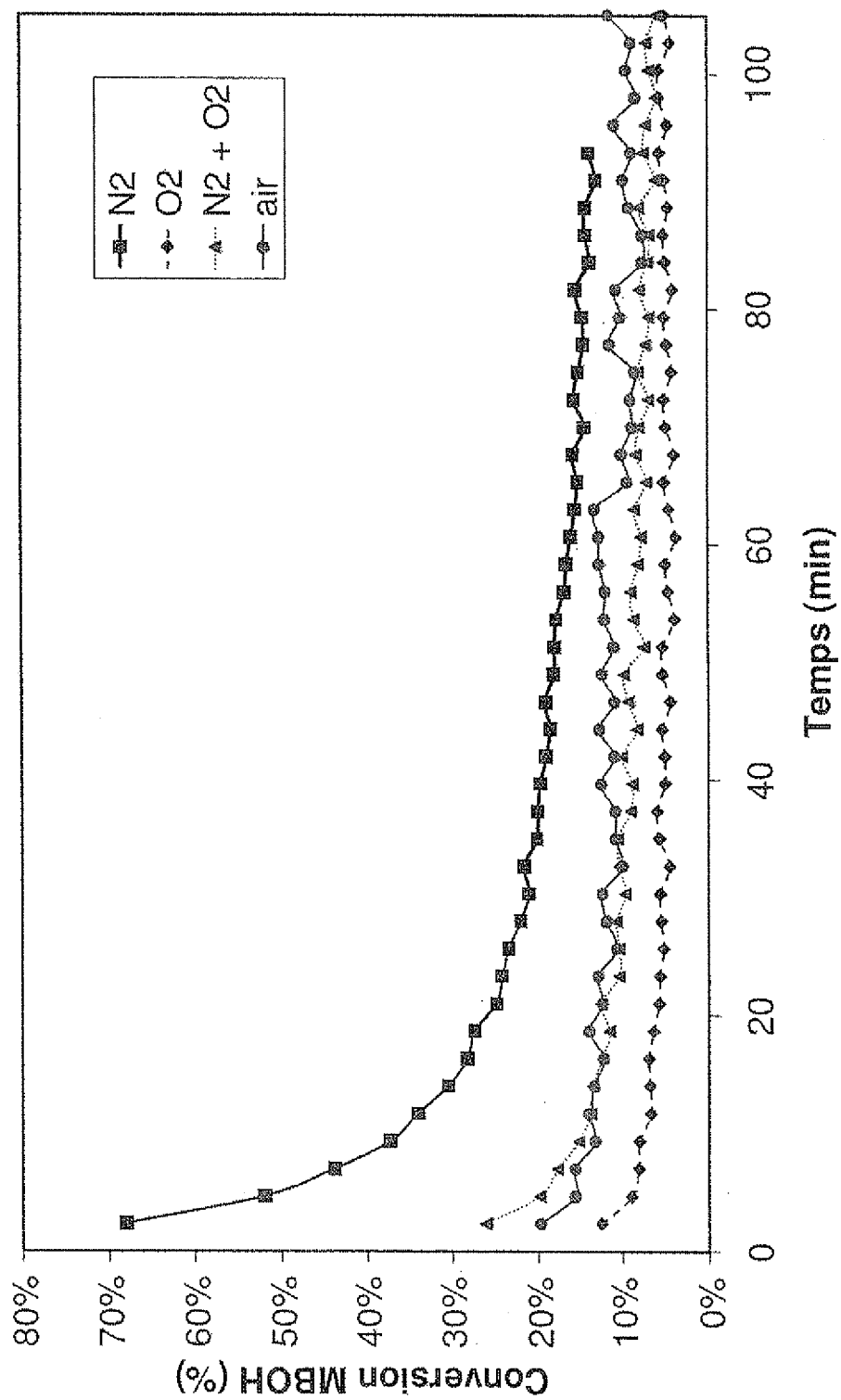
FIG. 3 gives a comparison of the conversion profiles of 2-methylbut-3-yn-2-ol as a function of time for ZnO samples obtained by decomposition of zinc carbonate, pretreated at 500° C. in $N_2$, $O_2$, $N_2/O_2$ or in air.

The dependence of the conversion of MBOH on the pretreatment atmosphere is more marked than with the commercial Kadox ZnO. Pretreatment in $N_2$ alone leads to the highest conversion (68% after two minutes, in contrast to only 12% for pretreatment in $O_2$) as shown in FIG. 3.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 10/01961, filed May 7, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalytic alcohol conversion method using a zinc oxide-based catalyst, comprising a thermal pretreatment stage of the zinc oxide-based catalyst in an oxygen-free inert and/or reducing atmosphere, at a temperature of at least 100° C., prior to the reaction stage, the pretreatment stage being carried out according to a thermal profile comprising at least one step at a temperature of 500° C., for at least 60 minutes, then a temperature descent down to alcohol conversion reaction temperature.

2. A method as claimed in claim 1, wherein the pretreatment stage is carried out at a temperature of at least 300° C.

3. A method as claimed in claim 1, wherein pretreatment is carried out in an atmosphere of nitrogen, argon and/or hydrogen.

4. A method as claimed in claim 1, wherein the alcohol is ethanol.

5. A method as claimed in claim 1, wherein the alcohol is 2-methylbut-3-yn-1-ol.

6. A method as claimed in claim 1, wherein the reaction stage is carried out at a temperature ranging between 100° C. and 500° C.

7. A method as claimed in claim 6, wherein the temperature ranges between 200° C. and 450° C.

8. A method as claimed in claim 1, wherein the zinc oxide is obtained by thermal decomposition of an organic zinc salt comprising zinc nitrate, zinc carbonate, zinc acetate, zinc citrate, zinc oxalate and/or zinc hydroxynitrate.

9. A method as claimed in claim 1, wherein the zinc oxide catalyst is obtained by thermal decomposition of an organic zinc salt consisting of zinc nitrate, zinc carbonate, zinc acetate, zinc citrate, zinc oxalate and/or zinc hydroxynitrate.

* * * * *